(12) United States Patent

Root et al.

(10) Patent No.: US 8,758,427 B2
(45) Date of Patent: Jun. 24, 2014

(54) ELONGATED EXPANDABLE MEMBER FOR OCCLUDING VARICOSE VEINS

(75) Inventors: Howard Root, Excelsior, MN (US);
James Murto, Maple Grove, MN (US);
Stephen Penegor, Watertown, MN (US);
Gregg Sutton, Maple Grove, MN (US)

(73) Assignee: Vascular Solutions, Inc., Minneapolis, MN (US)

( * ) Notice: Subject to any disclaimer, the term of this patent is extended or adjusted under 35 U.S.C. 154(b) by 363 days.

(21) Appl. No.: 13/310,503

(22) Filed: Dec. 2, 2011

(65) Prior Publication Data

US 2013/0144323 A1   Jun. 6, 2013

(51) Int. Cl.
*A61F 2/06* (2013.01)

(52) U.S. Cl.
USPC .......................................... 623/1.24; 606/194

(58) Field of Classification Search
CPC ................ A61L 31/145; A61L 31/146; A61B 17/12031; A61B 17/12109
USPC .......................... 606/194, 213; 623/1.24, 1.38
See application file for complete search history.

(56) References Cited

U.S. PATENT DOCUMENTS

| | | | |
|---|---|---|---|
| 4,755,184 A | 7/1988 | Silverberg | |
| 5,320,639 A | 6/1994 | Rudnick | |
| 5,456,693 A | 10/1995 | Conston et al. | |
| 5,522,840 A | 6/1996 | Krajicek | |
| 7,303,571 B2 | 12/2007 | Makower et al. | |
| 7,465,318 B2 | 12/2008 | Sennett et al. | |
| 7,582,110 B2 | 9/2009 | Case et al. | |
| 7,815,661 B2 | 10/2010 | Mirizzi et al. | |
| 7,842,054 B2 | 11/2010 | Greene, Jr. et al. | |
| 7,955,343 B2 | 6/2011 | Makower et al. | |
| 8,029,560 B2 | 10/2011 | Bates et al. | |
| 8,100,934 B2 | 1/2012 | Darnis et al. | |
| 8,128,682 B2 | 3/2012 | Case et al. | |
| 8,333,786 B2 | 12/2012 | Mirizzi et al. | |
| 2003/0153972 A1 | 8/2003 | Helmus | |

(Continued)

FOREIGN PATENT DOCUMENTS

| WO | WO-2010096717 A1 | 8/2010 |
|---|---|---|
| WO | WO-2013081768 A1 | 6/2013 |

OTHER PUBLICATIONS

"International Application Serial No. PCT/US2012/063101, International Search Report mailed Feb. 25, 2013", 6 pgs.

(Continued)

*Primary Examiner* — Victor Nguyen
(74) *Attorney, Agent, or Firm* — Schwegman, Lundberg & Woessner, P.A.

(57) ABSTRACT

Assemblies, kits, and methods for occluding a vascular vessel, such as a varicose vein, are disclosed. An assembly can include a removable inner member, a removable outer member, and an elongated expandable member positioned in a compressed form between portions of the inner and outer members. To facilitate their removal, one or both of the inner and outer members can include a handle coupled to a proximal end. The elongated expandable member can include a gelatin material or a collagen material that is configured, when wetted, to expand from a compressed first diametrical size to a second larger diametrical size within a time period of 5 minutes or less. At the second larger diametrical size, the gelatin or collagen material can occlude a vascular vessel for a period of at least 20 days without degrading.

11 Claims, 9 Drawing Sheets

(56) References Cited

U.S. PATENT DOCUMENTS

| | | |
|---|---|---|
| 2006/0212127 A1 | 9/2006 | Karabey et al. |
| 2006/0229668 A1 | 10/2006 | Prestezog et al. |
| 2006/0276882 A1 | 12/2006 | Case et al. |
| 2007/0166345 A1 | 7/2007 | Pavcnik et al. |
| 2007/0292472 A1 | 12/2007 | Paul et al. |
| 2007/0293932 A1 | 12/2007 | Zilla et al. |
| 2008/0243068 A1 | 10/2008 | Ramzipoor et al. |
| 2009/0069758 A1 | 3/2009 | Bates et al. |
| 2010/0106178 A1 | 4/2010 | Obermiller et al. |
| 2010/0274280 A1* | 10/2010 | Sawhney et al. .............. 606/213 |
| 2011/0005062 A1 | 1/2011 | Greene, Jr. et al. |
| 2011/0066183 A1 | 3/2011 | Sawhney et al. |
| 2011/0077683 A1 | 3/2011 | Huss |
| 2011/0152902 A1 | 6/2011 | Kurrus et al. |
| 2012/0245614 A1 | 9/2012 | Drasler |

OTHER PUBLICATIONS

"International Application Serial No. PCT/US2012/063101, Written Opinion mailed Feb. 25, 2013", 6 pgs.

* cited by examiner

ELONGATED EXPANDABLE MEMBER FOR OCCLUDING VARICOSE VEINS

TECHNICAL FIELD

This patent document pertains generally to occluding blood flow within a vascular vessel. More particularly, but not by way of limitation, this patent document pertains to assemblies, kits, and methods to treat varicose veins and varicosities associated with superficial reflux of a great or lesser saphenous vein or a branch superficial or perforator vein.

BACKGROUND

Vascular vessels are the conduits for circulating blood through a mammalian body. A vascular vessel that carries blood away from a heart is known as an artery. A vascular vessel that returns blood to the heart is known as a vein.

To assist blood flow, veins include venous valves. Each venous valve is located inside a vein and typically includes at least two valve leaflets that are disposed annularly along inside walls of the vein. These valve leaflets open to permit blood flow toward the heart and close, upon a change in pressure, to restrict the back flow or reflux of blood. When blood flows toward the heart, venous pressure forces the valve leaflets to move apart in a downstream flexing motion and create an open path for blood flow. The leaflets normally return to a closed position to restrict or prevent blood flow in a retrograde direction after the venous pressure is relieved. The leaflets, when functioning properly, extend radially inward toward one another such that the leaflet tips contact each other when the valve is closed.

On occasion, and for a variety of reasons including congenital valve or vein weakness, disease in the vein, obesity, pregnancy, or an occupation requiring long periods of standing or sitting, one or more valves in a vein may allow retrograde blood flow to occur. When a valve allows such retrograde flow, blood can collect in vessels beneath the valve and cause an increase in the venous pressure there. Venous valves that allow retrograde flow are known as incompetent venous valves. Incompetent venous valves can cause veins to bulge, can cause swelling in the patient's lower extremities, and can result in varicose veins. If left untreated, varicose veins can result in aching, pain, leg heaviness and swelling, fatigue, and aesthetic issues, among other things.

Surgical and non-surgical methods for treatment of varicose veins exist. An example non-surgical method for treatment of varicose veins is the placement of an elastic stocking around a patient's leg. The stocking can apply external pressure to the vein, forcing the vein walls radially inward and the leaflets into apposition. Another non-surgical treatment method is sclerotherapy, which involves the direct injection of a sclerosing or drug agent solution along the length of the varicose vein using a needle. The chemical solution can irritate the vein tissue, causing the lining of the vein to swell, harden, and eventually seal off.

An example surgical method for treatment of varicose veins includes bringing incompetent leaflets into closer proximity in hopes of restoring natural valve function. Methods for surgical constriction of an incompetent vein can include implanting a frame around the outside of the vessel, placing a constricting suture around the vessel, or other types of treatment to the outside of the vessel to induce vessel contraction. Other surgical treatment methods include: bypassing or replacing damaged venous valves with autologous sections of veins containing competent valves and vein stripping and ligation.

Recently, a number of methods have been suggested to treat varicose veins and venous valve leaflets with energy sources, such as radiofrequency ("RF") or laser energy. In one such method, valve leaflets can be fastened together with electrodes delivering RF energy. In another such method, a catheter or laser fiber having an electrode tip can be used to apply RF or laser energy to venous wall tissue causing localized heating and corresponding tissue destruction. After treatment of one venous wall section is complete, the catheter or laser fiber can be repositioned to treat a different venous wall section.

OVERVIEW

The present inventors recognize, among other things, that existing varicose vein treatments and structures are associated with limitations and drawbacks. For example, an elastic stocking placed around a patient's leg can be quite uncomfortable, especially in warm weather, and the stocking must be constantly worn to keep the leaflets in apposition. The elastic stocking can also affect the patient's physical appearance, potentially having an adverse psychological effect on him/her leading to removal of the stocking. Sclerotherapy can result in patient swelling due to agent injection and numerous needle pokes. Vein bypassing and vein stripping and ligation require at least one incision, a relatively long patient recovery time, have the potential for scarring, and numerous other risks inherent with surgery, such as those associated with the administration of anesthesia. Application of RF or laser energy requires expensive capital equipment (e.g., an energy source), vein insulation and compression means, and a dialing-in of energy and can cause thermal or perforation damage to a vessel of the patient.

The present assemblies, kits, and methods provide a new varicose vein treatment and delivery and implant structures. The treatment and structures are associated with minimal patient discomfort and a minimal risk of vessel perforation, are mechanically stable, resist migration and are cosmetically pleasing, do not require a capital equipment investment or insulation, and form part of a procedure that can be completed in a relatively fast manner. An example assembly can comprise a removable inner member, a removable outer member including an impermeable material, and an elongated expandable member positioned in a compressed form between portions of the inner and outer members. To facilitate their removal, one or both of the inner and outer members can include a handle coupled to their proximal end. The elongated expandable member can include a gelatin or collagen material that is configured, when wetted, to expand from a compressed first diametrical size to a second larger diametrical size within a time period of about 5 minutes or less. At the second larger diametrical size, the gelatin or collagen material can occlude a vessel for a period of at least 20 days without degradation of the occluding material, for example.

To better illustrate the assemblies, kits, and methods disclosed herein, a non-limiting list of examples is provided here:

In Example 1, an assembly for at least partial positioning within a vascular vessel comprises a removable inner member including a handle coupled to a proximal end portion, a removable outer member including an impermeable material, and an elongated expandable member positioned in a compressed form within the outer member and adjacent to portions of the inner member. The elongated expandable member can be configured to expand and occlude the vascular vessel following in situ separation and removal of the outer member.

In Example 2, the assembly of Example 1 is optionally configured such that the elongated expandable member is positioned in a compressed form between portions of the inner member and the outer member.

In Example 3, the assembly of any one or any combination of Examples 1 or 2 is optionally configured such that the elongated expandable member includes a gelatin or collagen material.

In Example 4, the assembly of Example 3 is optionally configured such that the gelatin or collagen material includes a degree of vapor cross-linking characterized by Lysine residuals of 1.5% or less.

In Example 5, the assembly of Example 4 is optionally configured such that the degree of cross-linking is configured to prevent the gelatin or collagen material from degrading for a period of at least about 20 days.

In Example 6, the assembly of any one or any combination of Examples 1-5 is optionally configured such that the elongated expandable member includes a density between 0.005 g/cm$^3$ and 0.010 g/cm$^3$.

In Example 7, the assembly of any one or any combination of Examples 1-6 is optionally configured such that the elongated expandable member includes a wicking agent selected from a salt or a sugar.

In Example 8, the assembly of any one or any combination of Examples 1-7 is optionally configured such that the elongated expandable member is configured to expand, when wetted, from a compressed first diametrical size to a second larger diametrical size, the second larger diametrical size at least about 5 times the first diametrical size.

In Example 9, the assembly of Example 8 is optionally configured such that the elongated expandable member includes a length of at least about 10 centimeters, and wherein the elongated expandable member completely expands in situ from the first diametrical size to the second larger diametrical size within a time period of about 5 minutes or less.

In Example 10, the assembly of any one or any combination of Examples 8 or 9 is optionally configured such that the second larger diametrical size of the elongated expandable member is substantially equal to a pre-wetted size of the member before being compressed within the outer member.

In Example 11, the assembly of any one or any combination of Examples 1-10 is optionally configured such that the elongated expandable member includes an antimicrobial agent selected from a silver compound, chlorhexidine, an antibiotic, or an iodine-containing agent.

In Example 12, the assembly of any one or any combination of Examples 1-11 is optionally configured such that the elongated expandable member includes a pH adjuster. The pH adjuster includes a concentration resulting in the member having a pH greater than 5.7 and is selected from hydrochloric acid, sodium hydroxide, or a buffer.

In Example 13, a kit for at least partial positioning within a vascular vessel comprises a needle, a guide wire, the assembly of any one or any combination of Examples 1-12, and instructions for using the assembly to insert the elongated expandable member within and occlude a varicose vein.

In Example 14, the kit of Example 13 is optionally configured such that the sheath includes a tear-away member and a dilator.

In Example 15, the kit of any one or any combination of Examples 13 or 14 is optionally configured such that the instructions teach using the assembly to insert the elongated expandable member within and occlude a great saphenous vein or a lesser saphenous vein.

In Example 16, the kit of any one or any combination of Examples 13-15 is optionally configured such that the instructions teach using the assembly to insert the elongated expandable member within and occlude a branch superficial or a perforator vein.

In Example 17, an assembly for at least partial positioning within a vascular vessel comprises a removable inner tubular member, a removable outer member including an impermeable material, and an elongated expandable member having a length of at least about 10 centimeters and positioned in a compressed form between the inner tubular member and the outer member. The elongated expandable member can include one or more cross-linked bonds and a wicking agent allowing the member to expand and occlude the vascular vessel for a period of at least about 20 days.

In Example 18, the assembly of Example 17 is optionally configured such that the elongated expandable member includes a compressed to expanded size ratio of at least about 1:5.

In Example 19, the assembly of any one or any combination of Examples 17 or 18 is optionally configured such that the elongated expandable member expands from the compressed form to occlude the vascular vessel within a time period of about 5 minutes or less.

In Example 20, a method comprises inserting an elongated expandable member, compressed about, around, or adjacent to an inner tubular member and covered by an impermeable outer member, into a vascular vessel, and separating and removing the outer member in situ. The removal of the outer member allows the elongated expandable member to expand from a compressed first diametrical size to a second larger diametrical size, and occlude the vascular vessel.

In Example 21, the method of Example 20 optionally comprises removing the inner tubular member at a time after the elongated expandable member expands from the first diametrical size.

In Example 22, the method of any one or any combination of Examples 20 or 21 is optionally configured such that inserting the elongated expandable member into the vascular vessel includes guiding an inner lumen of the inner tubular member over a guide wire.

In Example 23, the method of any one or any combination of Examples 20-22 is optionally configured such that inserting the elongated expandable member into the vascular vessel includes guiding a protective tip over a guide wire.

In Example 24, the method of any one or any combination of Examples 20-23 is optionally configured such that inserting the elongated expandable member into the vascular vessel includes inserting an elongated expandable member, having a length of at least about 10 centimeters, into a great saphenous vein or a lesser saphenous vein.

In Example 25, the method of any one or any combination of Examples 20-23 is optionally configured such that inserting the elongated expandable member into the vascular vessel includes inserting an elongated expandable member, having a length of at least 1 centimeter, into a branch superficial or perforator vein.

In Example 26, the method of any one or any combination of Examples 20-25 is optionally configured such that inserting the elongated expandable member into the vascular vessel includes inserting a gelatin or collagen material, having a degree of vapor cross-linking characterized by Lysine residuals of 1.5% or less and a density of between 0.005 g/cm$^3$ and 0.010 g/cm$^3$, into a vascular vessel.

In Example 27, the method of any one or any combination of Examples 20-26 is optionally configured such that separating and removing the outer member includes removing the outer member in a proximal-to-distal direction.

In Example 28, the method of any one or any combination of Examples 20-27 is optionally configured such that allowing the elongated expandable member to expand includes increasing an outer diametrical size of the elongated expandable member a multiple of at least 5 within a time period of about 5 minutes or less.

In Example 29, the method of any one or any combination of Examples 20-28 is optionally configured such that allowing the elongated expandable member to expand includes preventing degradation of the occlusive member for a period of at least about 20 days.

In Example 30, the assembly, kit, or method of any one or any combination of Examples 1-29 is optionally configured such that all elements or options recited are available to use or select from.

These and other examples and features of the present assemblies, kits, and methods will be set forth in part in the following Detailed Description. This Overview is intended to provide non-limiting examples of the present subject matter—it is not intended to provide an exclusive or exhaustive explanation. The Detailed Description below is included to provide further information about the present assemblies, kits, and methods.

BRIEF DESCRIPTION OF THE DRAWINGS

In the drawings, like numerals can be used to describe similar elements throughout the several views. Like numerals having different letter suffixes can be used to represent different views of similar elements. The drawings illustrate generally, by way of example, but not by way of limitation, various embodiments discussed in the present document.

DETAILED DESCRIPTION

Varicose veins are quite common for both men and women. In fact, over 40 million people have varicose veins in the U.S. alone—with 50% of the population, age 50 and older, suffering from varicose veins. Some risk factors related to the manifestation of varicose veins include: heredity, age, gender, obesity, pregnancy, and prolonged standing or sitting. Symptoms related to varicose veins can vary from mild to severe with aching, pain, leg heaviness and swelling, fatigue, and aesthetic issues varying based on the severity of the disease. More severe symptoms include deep vein thrombosis, pulmonary embolism, and ulceration, which can lead to serious problems and even death if left untreated.

The present inventors recognize that treatment of varicose veins is important, and further recognize that existing varicose vein methods of and structures for treatment are associated with limitations and drawbacks. A new varicose vein treatment and delivery and implant structures that are associated with minimal patient discomfort and a minimal risk of vessel perforation, are mechanically stable, resist migration and are cosmetically pleasing, do not require a capital equipment investment or insulation, and form part of a procedure that can be completed in a relatively fast manner are disclosed in this patent document.

Figure 1:
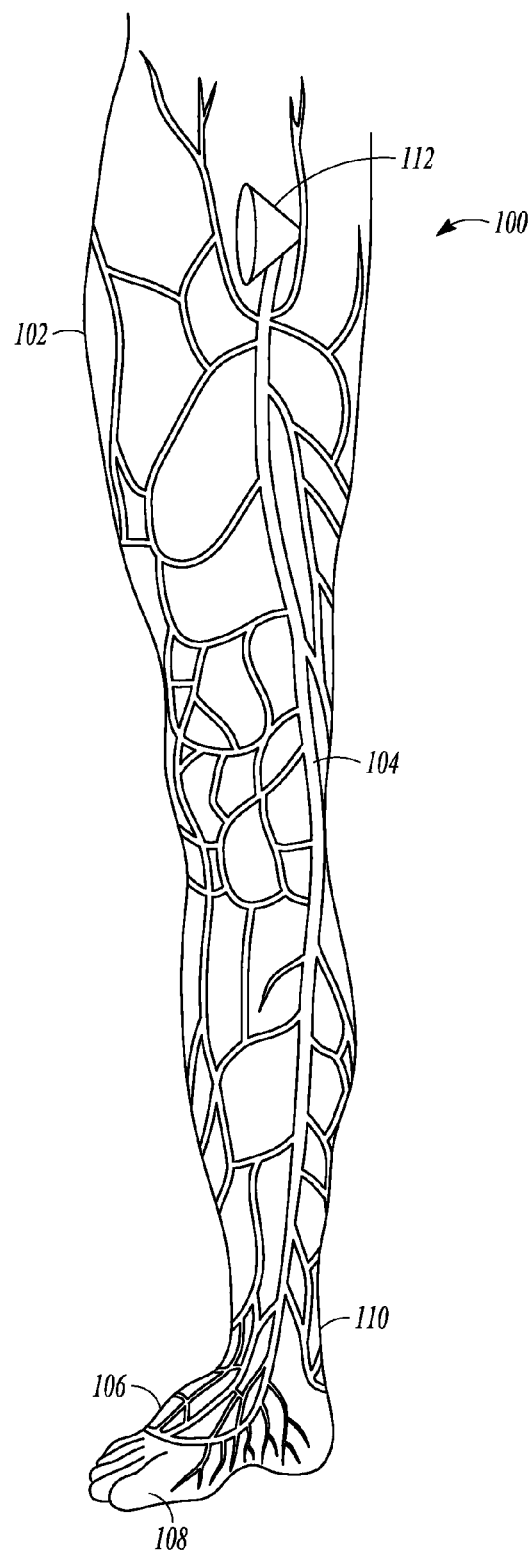
FIGS. 1 and 2 illustrate vessel structures of a human leg, which provide suitable environments in which the present assemblies, kits, and methods for occluding a vascular vessel can be used, as constructed in accordance with at least one embodiment.
Figure 2:
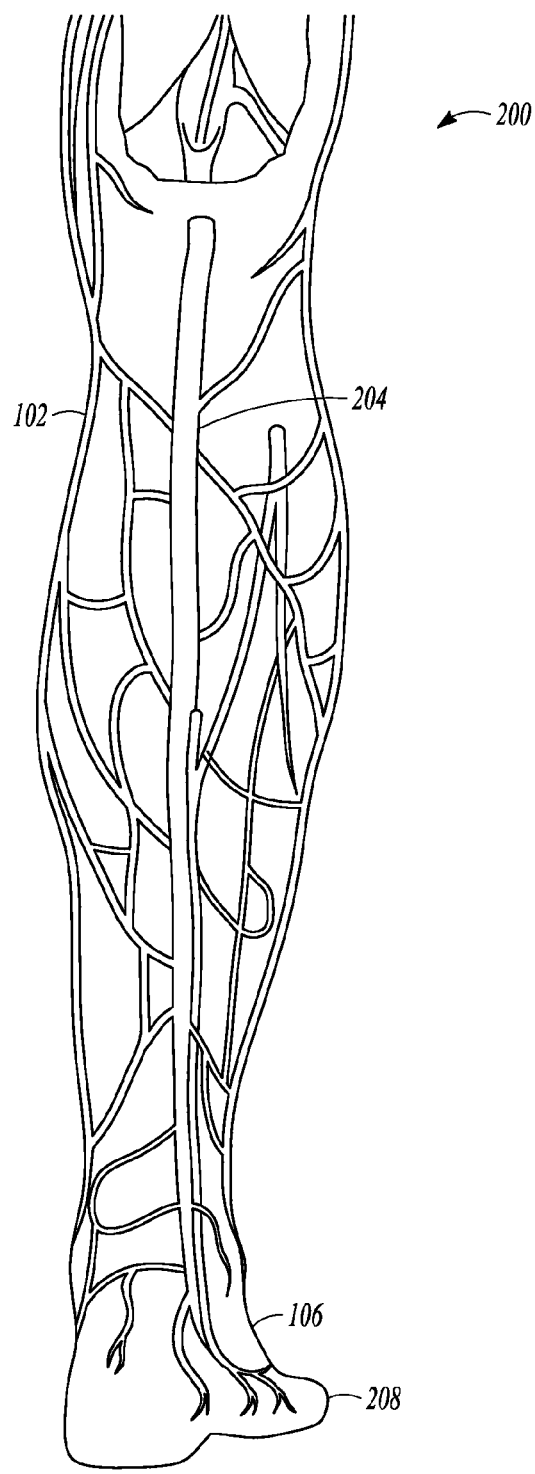

FIGS. 1 and 2 illustrate vessel structures 100, 200 of a human leg 102, which provide suitable environments in which the present assemblies, kits, and methods for occluding a vascular vessel can be used. Among other things, FIG. 1 illustrates a great saphenous vein 104, which is a large superficial vein of an anterior side of the leg 102. The great saphenous vein 104 originates from where a dorsal vein of a large toe 108 merges with a dorsal venous arch of a foot 106. After passing anterior to a medial malleolus 110, the vein 104 runs up a medial side of the leg 102. At the knee, the great saphenous vein 104 runs over a femur bone and then extends medially on an anterior surface of the thigh until it joins with a femoral vein 112.

FIG. 2 illustrates a lesser saphenous vein 204, which is a large superficial vein of a posterior side of the leg 102. The lesser saphenous vein 204 originates from where a dorsal vein of the smallest toe 208 merges with the dorsal venous arch of the foot 106. The lesser saphenous vein 204 runs along the posterior surface of the leg 102, passes between heads of a gastrocnemius muscle, and drains into a popliteal vein at or above the knee joint.

Figure 3:
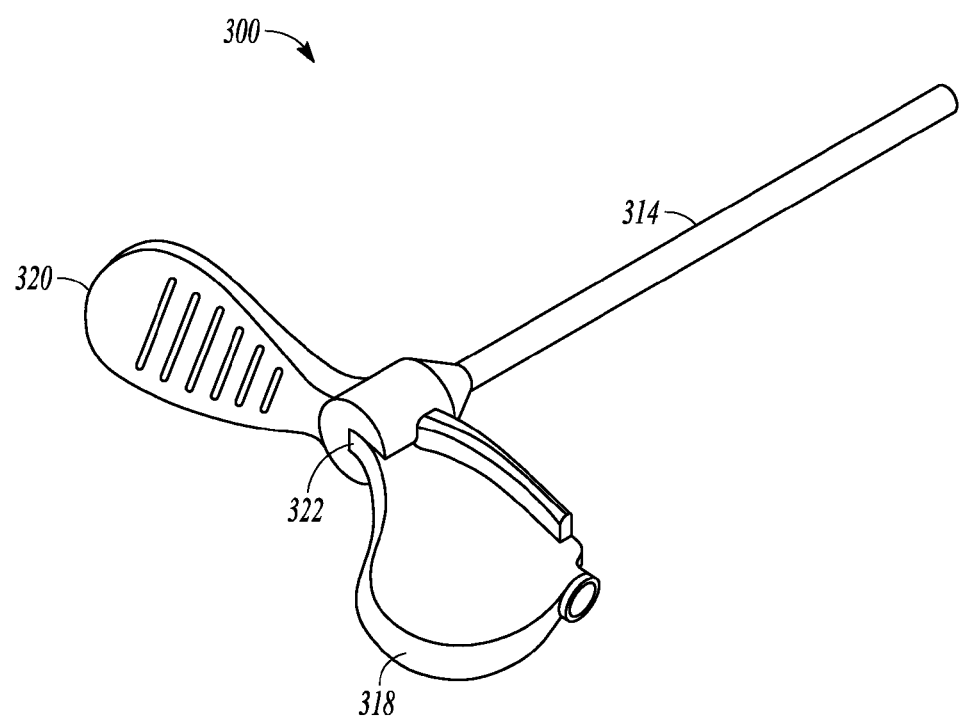
FIG. 3 illustrates an isometric plan view of an example assembly for occluding a vascular vessel, as constructed in accordance with at least one embodiment.
Figure 5:
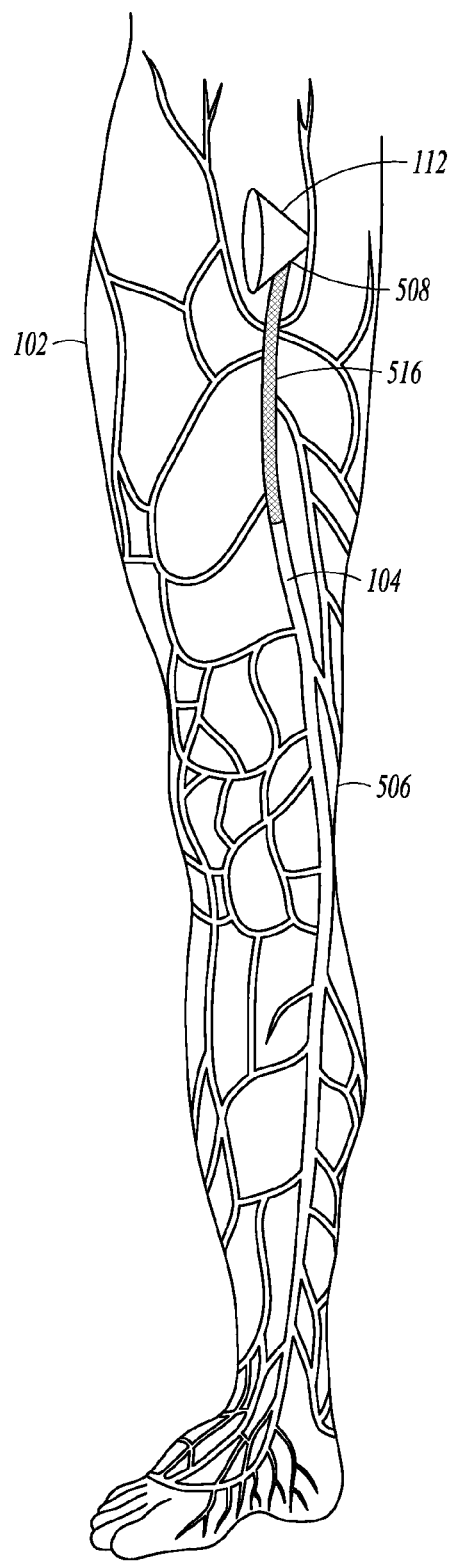
FIG. 5 illustrates an elongated expandable member of an assembly located in and occluding a great saphenous vein, as constructed in accordance with at least one embodiment.

In accordance with the present assemblies, kits, and methods, one or more portions of the great saphenous vein 104, the lesser saphenous vein 204, or a branch superficial or perforator vein can be occluded as illustrated in FIG. 5. Desirably, the occlusion can be effective to prevent reflux of venous blood in a downward direction, thereby treating varicosities that commonly occur in lower portions of the leg 102. With reference to FIGS. 3 and 5, occlusion of a portion of the great saphenous vein 104 can be achieved by deploying an elongated expandable member, initially positioned in a compressed form between portions of inner and outer members of an assembly 300, into the vein 104.

FIG. 3 illustrates an isometric plan view of an example assembly 300 for occluding a vascular vessel such as a great or lesser saphenous vein or a branch superficial or perforator vein, as constructed in accordance with at least one embodiment. The assembly 300 can comprise a removable inner member, a removable outer member 314, and an elongated expandable member positioned in a compressed form between portions of the inner member and the outer member 314. The inner member can, for example, include a polyimide tube material and the outer member 314 can include an impermeable polytetrafluoroethylene material. The inner and outer members can include a handle 318, 320 respectively coupled to their proximal ends. Adjacent inner surfaces of the handles 318, 320 can form a snap-fit connection 322. The snap-fit connection 322 can be separated when desired by a caregiver user.

The elongated expandable member is configured to expand and occlude a vascular vessel following in situ separation and removal of the outer member 314. The elongated expandable member can include a biodegradable gelatin or collagen material having a sponge- or foam-like structure. The sponge- or foam-like structure allows the elongated expandable member to be compressed for insertion into the vascular vessel and, following removal of the outer member 314, allows for absorption of vessel fluid. The intake of fluid causes the elongated expandable member to expand and provide mechanical fixation inside the vessel and also to block the flow of fluid, such as blood, through the vessel. Optionally, the elongated expandable member can include antibiotics or other desired drugs and can have the property of promoting tissue in-growth.

A kit can comprise the assembly 300, a needle, a guide wire, and instructions for using the assembly 300 to insert the elongated expandable member within a vascular vessel such as a great (FIG. 1) or lesser (FIG. 2) saphenous vein or a branch superficial or perforator vein. The elongated expandable member can have a variety of lengths including about 10 centimeters ("cm"), about 25 cm, about 50 cm, or about 75 cm and longer. In an example, the elongated expandable member can have a shorter length, such as about 1 cm or 2 cm for occlusion of a branch superficial or perforator vein. In examples where the assembly 300 has low pushability or column strength, a delivery sheath can be included in the kit and used to deploy the assembly 300 using an over-the-guide wire method. In some examples, the sheath can include a tear-away member and a dilator.

Figure 4:
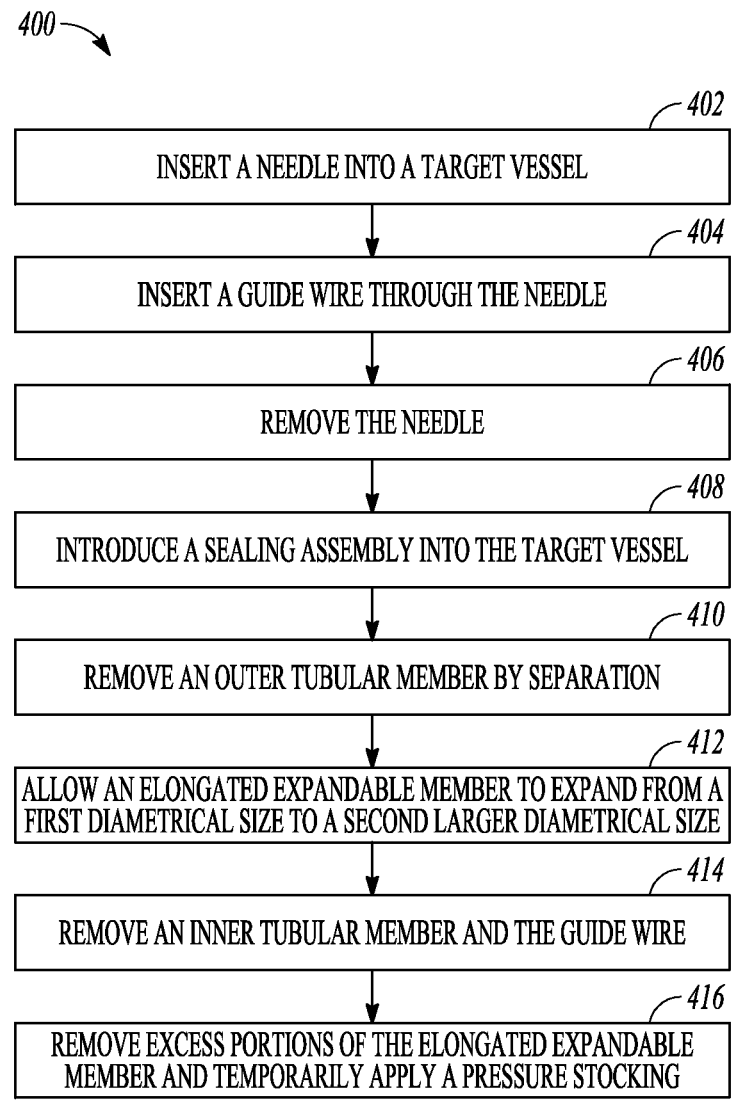
FIG. 4 illustrates an example method of using an assembly or kit for occluding a vascular vessel, as constructed in accordance with at least one embodiment.

FIG. 4 illustrates an example method 400 of using an assembly or kit for occluding a vascular vessel as conceived by the present inventors. The method can be implanted by first inserting a needle into a target vessel in operation 402. As an alternative to a vessel, the target can be a hollow body organ, solid tissue location, body cavity, or the like. A guide wire, such as a 0.018 inch wire, can then be inserted through an inner lumen of the needle in operation 404 and into the target vessel, thereby providing a "railway" to the vessel. Once the guide wire is in place, the needle can be removed in operation 406.

The assembly can be introduced into the target vessel in operation 408 using an over-the-guide wire technique, with the guide wire passing through an inner lumen of an inner member of the assembly. Portions of the assembly, particularly the elongated expandable member, can be sufficiently compressed so that its outer diameter is smaller than the lumen of a delivery sheath for ease of insertion. Optionally, ultrasound or x-ray techniques can be used to visualize a distal tip of the assembly during vessel introduction, such as for monitoring a vessel depth of the assembly.

Once introduced into the target vessel, an impermeable outer member of the assembly can be removed in operation 410, such as by splitting, peeling, cutting, or otherwise separating it along a split, cut line, score line, linear orientation, or other structure allowing linear separation. In an example, a handle attached to a proximal end of the inner member can be held in place while a handle attached to a proximal end of the outer member is moved in a direction away from inner member's handle. This relative handle movement can cause a blade integrated in the inner member's handle to contact and cut the impermeable outer member in a proximal-to-distal direction. In an alternative example, proximal pulling of a cutting wire, which is positioned between the elongated expandable member and the outer member, can allow for separation of the outer member in a distal-to-proximal direction. After the outer member is removed, the inner member and the elongated expandable member remain. The elongated expandable member is then free to absorb vessel fluid and expand to provide mechanical fixation inside the vessel and also to block the flow of fluid, such as blood, through the vessel in operation 412. In some examples, the elongated expandable member increases in outer diametrical size by a multiple of at least 5 within a time period of 5 minutes or less.

After the elongated expandable member fully expands, the inner member and the guide wire can be removed in operation 414. In operation 416, excess portions of the elongated expandable member, if any, can be removed and a pressure stocking can be temporarily applied around a patient's skin in the vicinity of the now occluded target vessel. In various examples, the elongated expandable member is configured to prevent its degradation for a period of at least 20 days.

FIG. 5 illustrates an elongated expandable member 516 of an assembly located in and occluding a portion of a great saphenous vein 104 of a leg 102, as constructed in accordance with at least one embodiment. In this example, the elongated expandable member 516 is placed between a point 506 near a medial side of the leg 102 to a point 508 near a junction between the great saphenous vein 104 and a femoral vein 112.

Initially disposed in a compressed configuration to ease vessel introduction, the elongated expandable member 516 is configured to quickly expand upon removal of an outer impermeable member in situ. The elongated expandable member 516, when wetted within the vein 104, expands from a first diametrical size to a second larger diametrical size. In various examples, the second larger diametrical size is at least 5 times or at least 10 times the first diametrical size. In some examples, the second diametrical size is substantially equal to a pre-wetted size of the member before being compressed and positioned between portions of an assembly inner member and outer member. Advantageously, the elongated expandable member 516 includes a length of at least 10 cm and can include a cylindrical outer surface. The elongated structure and cylindrical outer surface can provide a large contact surface between the elongated expandable member 516 and the walls of the vein 104 to inhibit movement of the member 516 under venous pressure. Inhibiting the risk of member migration by way of an elongated structure is an important benefit over small liquid-based suspension particles, such as those associated with Pfizer's GELFOAM® product and Johnson and Johnson's SURGIFOAM® product.

Figure 6:
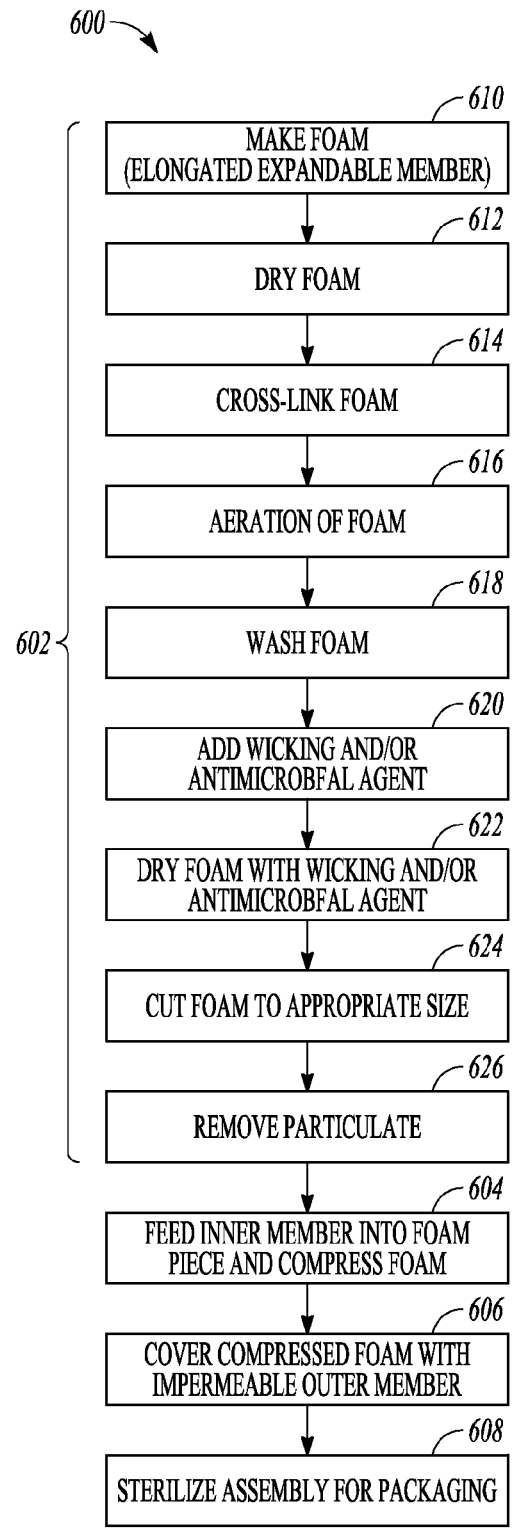
FIG. 6 illustrates an example method of manufacturing an assembly for occluding a vascular vessel, as constructed in accordance with at least one embodiment.

FIG. 6 illustrates an example method 600 of manufacturing an assembly for occluding a vascular vessel, as constructed in accordance with at least one embodiment. The method includes manufacturing an elongated expandable member 602, compressing the elongated expandable member onto an inner member 604, covering the compressed elongated expandable member with an impermeable outer member 606, and sterilizing the assembly for packaging 608.

Manufacturing the elongated expandable member 602 can include creating a sponge- or foam-like matrix structure having a relatively low density, large pore size, high degree of cross-linking, basic pH level, large compression ratio, and fast swell time when wetted.

In operation 610, a sheet of expandable gelatin can be treated to initiate the manufacture of the elongated expandable member 602. In some examples, the elongated expandable member can include treated reconstituted or naturally-derived collagenous materials to promote cellular growth within the member, thereby promoting permanent closure of an occluded passageway. Through proper treatment, the elongated expandable member can be configured to expand by at least about 5, at least about 6, at least about 7, at least about 8, at least about 9, at least about 10, and up to about 15 times its compressed diameter, or more. In some examples, the elongated expandable member is capable of expansion to its original, pre-compressed diameter. The magnitude of the expansion can be tailored by, among other things, varying the concentration of a pH adjuster, water, an oakes foamer, and the exposure time of these substances or the gelatin or collagen to control variables. In an example, the gelatin is treated with a pH adjuster selected from hydrochloric acid, sodium hydroxide, or a buffer in a concentration resulting in the gelatin matrix having a pH greater than 5.7. In an example, the treated gelatin matrix has a density between 0.005 g/cm$^3$ and 0.010 g/cm$^3$ and exhibits relatively large pore sizes.

The treated gelatin can be dried sufficiently in operation 612 to stabilize the matrix. Drying of the gelatin matrix can involve high flow of dehumidified air or vacuum drying at ambient or elevated temperatures. The drying procedure can reduce the liquid (e.g., water) content of the gelatin matrix to less than about 20% by weight, and more preferably, less than about 10% by weight.

Cross-linking can be used in operation 614 to impart desirable compression and expansion properties to the gelatin matrix. For example, cross-linking of a later compressed matrix can promote re-expansion of the matrix after implantation into a patient's vessel. The amount of added cross-linking within the gelatin matrix can be selected depending upon a desired treatment regime (e.g., occlusion duration or swell time for vessel fixation). In many examples, the gelatin matrix is cross-linked to complete an in situ expansion process over the course of minutes and prevent its degradation for at least 20 days, at least 30 days, and up to at least 90 days, or more. Cross-linking bonds can be initiated by the inclusion of formaldehyde or glutaraldehyde in vapor or liquid form, for example. Other cross-linking agents that can be used in vapor or liquid formulations include: isothiocyanates, isocyanates, acyl azides, NHS Esters, aldehydes, epoxides, carbodiimides, anhydyrids, genipin, and combinations thereof. The amount of cross-linking can be determined using DSC testing, for example, and numerically reported as Lysine residuals. A smaller Lysine residuals percentage represents a higher degree of cross-linking. In an example, the gelatin matrix includes Lysine residuals of 1.5% or less. In operations 616 and 618, the cross-linked gelatin matrix can be aerated and washed to reduce residuals of formaldehyde or other cross-linking agents.

A formulation including a wicking or wetting agent can be made in operation 620 and added to the cross-linked gelatin matrix. The wicking agent is a biocompatible substance that facilitates or enhances hydration and/or lubrication of the gelatin matrix when implanted in a target vessel. In an example, the wicking agent can be selected from a salt (e.g., sodium chloride) or a sugar. Other suitable wicking agents include polysaccharides, polyoxyalkylenes, glycerin, and water soluble polymers. Optionally, an antimicrobial agent can also be added to the gelatin matrix to destroy or interrupt microbial development and pathogenic actions. In an example, the antimicrobial agent can be selected from silver compounds, chlorhexidine, antibiotics, iodine-containing agents, and certain heavy metals. Experimental results have shown that the use of an antimicrobial agent (e.g., a silver compound) can result in a greater than 4 log reduction in bacterial contamination. The wicking formulation and optionally, the antimicrobial agent, can be dried into the gelatin matrix in operation 622. In an example, a freeze drying process is used in operation 622. The freeze drying can be performed at varying air pressures, matrix temperatures, and shelf temperatures for a period of days. Other suitable drying process include: air drying, vacuum drying, oven drying, and lyophilization. The drying procedure can reduce the liquid content of the gelatin matrix to less than about 10% by weight, and more preferably, less than about 1-2% by weight.

The cross-linked gelatin matrix including a wicking agent and optionally an antimicrobial agent can be cut (e.g., tore, grinded, sheared, etc.) to a desired size in operation 624. The cutting process can be manual or automated. In operation 636, particulate can be removed from the matrix using a vacuum or air brushing process and can complete the manufacturing of the elongated expandable member 602.

In operation 604, an inner member of the assembly can be fed into a portion of the elongated expandable member, and the elongated expandable member can be compress onto an outer surface of the inner member. Compression forces can be applied so as to achieve a desired density or configuration, and can be applied in one, two, or three dimensions, including radially. When processed in this manner, upon removal of the compression force, the elongated expandable member can be stabilized structurally and remains in a dense and compacted state until contacted with a liquid susceptible to absorption by the matrix, for example body fluids. The pores of the elongated expandable member can be retained at a volume substantially reduced from their maximum volume, but can return to a partially or fully expanded state when the matrix is wetted. In an example, the pre-compressed elongated expandable member can have a generally square shape. In an example, the compressed elongated expandable member can have a generally cylindrical shape with a generally circular cross section, and can have a diameter approximating that or smaller than that of a delivery sheath through which it is to be passed. In an example, the compression forces can cause a 10-to-1 diameter change of the elongated expandable member.

An impermeable outer member can be applied over the compressed elongated expandable member in operation 606 to prevent premature expansion when the assembly is introduced into a vessel. Finally, in operation 608, the assembly including the inner member, the elongated expandable member, and the outer member can be sterilized for packaging. The sterilization process can be completed using one or more of irradiation ("E-beam"), gamma sterilization, or dry heat sterilization. Experimental results have shown that a combination of an E-beam process followed by a heat process can result in a greater than 4 log reduction in viral contamination.

Figure 7:
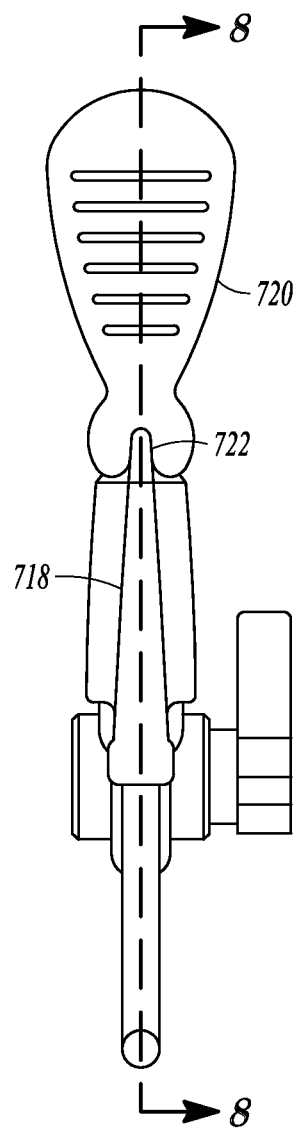
FIG. 7 illustrates a proximal end view of an example assembly for occluding a vascular vessel, as constructed in accordance with at least one embodiment.

FIG. 7 illustrates a proximal end view of an example assembly 700 for occluding a vascular vessel, as constructed in accordance with at least one embodiment. The assembly 700 can comprise a removable inner member, a removable outer member, and an elongated expandable member positioned in a compressed form between portions of the inner and outer members. The inner and outer members can each include a handle 718, 720 respectively coupled to their proximal ends. Adjacent inner surfaces of the handles 718, 720 can form a snap-fit connection 722, which can be separated when desired by a caregiver user.

Figure 8:
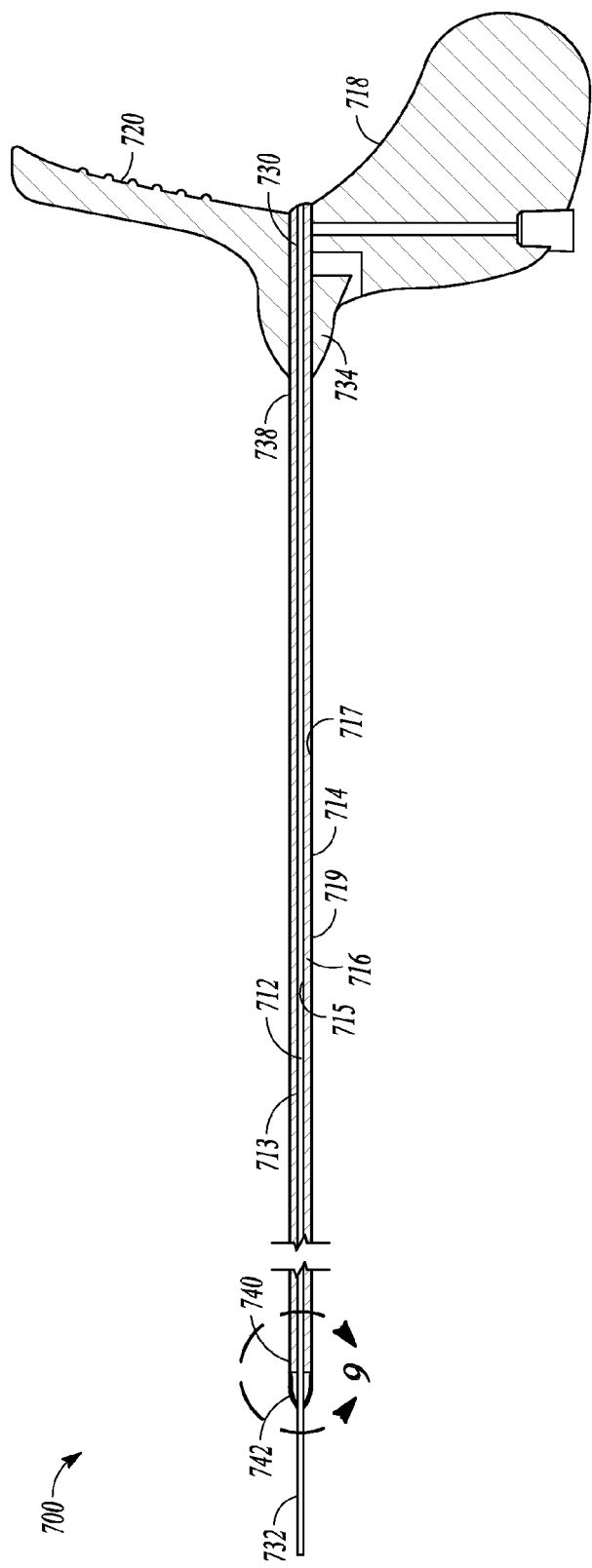
FIG. 8 illustrates a side cross-sectional view of an example assembly for occluding a vascular vessel, as constructed in accordance with at least one embodiment.

FIG. 8 illustrates a side cross-sectional view of the example assembly 700, such as along line 8-8 of FIG. 7. Moving from inside-out, the assembly 700 can include an inner member 712 having a longitudinal outer surface 713, an elongated expandable member 716 having a longitudinal inner surface 715 compressed onto the longitudinal outer surface 713 of the inner member 712, and an outer member 714 having a longitudinal inner surface 717 surrounding a longitudinal outer surface 719 of the elongated expandable member 716. Each of the inner member 712, the elongated expandable member 716, and the outer member 714 can extend from a proximal end to a distal end, with the elongated expandable member 716 positioned in a compressed form between the longitudinal inner surface 717 of the outer member 714 and the longitudinal outer surface 713 of the inner member 712.

The inner member 712 can extend from a proximal end 730 to a distal end 732 and can have a length longer than both the elongated expandable member 716 and the outer member 714. The inner member 712 can include a polyimide material having a tubular configuration for receiving a guide wire during a vessel introduction process. The proximal end 730 can be attached to a handle 718 including an integrated blade 734. The blade 734 can be used to cut the outer member 714 in a proximal-to-distal direction. Optionally, a side-arm member can be attached to the proximal end 730 to provide access to an introduction channel of the inner member 712. An infusion of fluid into the introduction channel by way of the side-arm member can function to flush the contents of the channel.

The outer member 714 extends from a proximal end 738 to a distal end 740. The outer member 714 can have a length longer than the elongated expandable member 716 but less than the inner member 712. The outer member 714 can include an impermeable polytetrafluoroethylene material and a protective tip 742 located at the distal end 740. The protective tip 742 can function to seal and prevent premature expansion of the elongated expandable member 716. Optionally, the protective tip 742 can include an x-ray visible material to guide introduction of the assembly 700 to a desired depth with a target vessel. The proximal end 738 can be attached to a handle 720 and moved in a direction away from handle 718 when a caregiver user desires to cut and remove the outer member 714.

The elongated expandable member 716 can be positioned between and sealed by the inner member 712 and the outer member 714. The elongated expandable member 716 is initially deployed in a radially compressed configuration to facilitate its delivery through vasculature and within a delivery sheath. After reaching a desired implantation site, the outer member 714 can be separated and removed, thereby allowing the elongated expandable member 716 to radially expand to an operative configuration in which the outer surface of the member 716 engages surrounding vessel walls. Post-expansion, the elongated expandable member 716 can block the conduit of the vessel and prevent blood from flowing therethrough.

Figure 9:
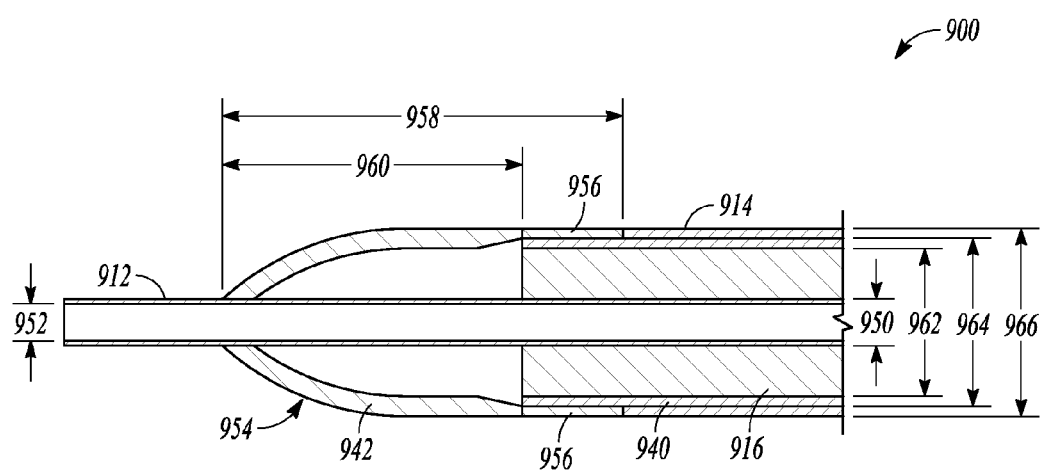
FIG. 9 illustrates a side cross-sectional view of a distal end portion of an assembly for occluding a vascular vessel, as constructed in accordance with at least one embodiment.

FIG. 9 illustrates a side cross-sectional view of a distal end portion of an assembly 900 for occluding a vascular vessel, as constructed in accordance with at least one embodiment. The assembly 900 includes an inner member 912, an elongated expandable member 916, and an outer member 914.

The inner member 912 can longitudinally extend beyond distal ends of both the outer member 914 and the elongated expandable member 916. In an example, the inner member 912 can include an outer diameter 950 of about 0.023 inches and an inner diameter 952 of about 0.022 inches.

A distal end 940 of the outer member 914 can include a protective tip 942. The protective tip 942 can include a radius of curvature 954 of about 0.175 inches on its outer surface to facilitate introduction of the assembly 900 includes a target vessel. The protective tip 942 can also include a rim protrusion 956 on its proximal end for coupling with the distal end 940 of the outer member. In an example, the protective tip 942 can include a main body length 960 of about 0.150 inches and a rim protrusion length of about 0.050 inches. Together, the main body and the rim protrusion can include a length 958 of about 0.200 inches. In an example, the rim protrusion can include a thickness of about 0.010 inches. In an example, the outer member 914 can include an inner diameter 962 of about 0.070 inches and an outer diameter 964 of 0.083 inches in the region of the rim protrusion 956 and a diameter 966 of about 0.093 inches proximal of the rim protrusion.

The elongated expandable member 916 can be compressed and positioned between the inner diameter 962 of the outer member 914 and the outer diameter 950 of the inner member 912. In an alternative example, the elongated expandable member 916 can be positioned within the outer member 914 and adjacent to the inner member 912, with the inner member 912 positioned between the inner diameter of the outer member 914 and an outer diameter of the elongated expandable member 916. In an example, the elongated expandable member 916 and the inner member 912 can be longitudinally positioned side-by-side (i.e., outer diametrical surface-by-outer diametrical surface) within the outer member 914.

Experimental Results:

Laboratory experiments were conducted to help quantify properties of example elongated expandable members, as conceived by the present inventors. In these experiments, elongated expandable members were manufactured using the teachings associated with FIG. 6. Each elongated expandable member was designed to occlude a vascular vessel (e.g., a varicose vein) by occupying the vessel's full cross-section and exerting sufficient radial pressure and friction on surrounding vessel walls to remain in place even when subjected to vessel (e.g., venous) pressures.

1. Experiment 1:

In this experiment, Lysine residuals of an elongated expandable member were explored relative to Lysine residuals of Pfizer's GELFOAM® product. The Lysine residuals were completed by hydrolysis of a sample sponge matrix from each product and running the sample on mass spectrometry.

TABLE 1

Experimental results showing that the present elongated expandable member exhibits lower Lysine residuals than a commercially available foam product.

| Product | Lysine Residuals (%) |
| --- | --- |
| Elongated expandable member | 1.1 |
| Pfizer's GELFOAM ® product | 1.7 |

2. Experiment 2:

In this experiment, the pH of an elongated expandable member including 0.03% sodium chloride and an elongated expandable member including 0.03% sodium chloride and 100 parts per million ("ppm") of silver were explored relative to the pH of Pfizer's GELFOAM® product.

TABLE 2

Experimental results showing that the present elongated expandable members include a higher (more basic) pH than a commercially available foam product.

| Product | pH |
| --- | --- |
| Elongated expandable member including 0.03% sodium chloride and 100 ppm of silver | 6.55 |
| Elongated expandable member including 0.03% sodium chloride | 5.93 |
| Pfizer's GELFOAM ® product (at saturation point) | 4.64 |

3. Experiment 3:

In this experiment, the pepsin digestion of an elongated expandable member was explored relative to the pepsin digestion of Pfizer's GELFOAM® product and the United States Pharmacopeia ("USP") sponge requirement. Pepsin is a digestive protease that degrades gelatin. The length of time it takes to degrade a wetted gelatin sponge relates to a degree of cross-linking present in a sample.

TABLE 3

Experimental results showing that the present elongated expandable member includes a longer pepsin digestion time than a commercially available foam product and the USP sponge requirement.

| Product | Time |
| --- | --- |
| Elongated expandable member | greater than 3 days |
| Pfizer's GELFOAM ® product | approximately 15 minutes |
| USP sponge requirement | less than or equal to 75 minutes |

4. Experiment 4:

In this experiment, a compression ratio of an elongated expandable member was explored relative to a compression ratio of Pfizer's GELFOAM® product. The compression ratio was calculated by comparing a sample sponge size for each product prior to compression and after compression. A standardized sample size of each product was prepared (1 cm×1 cm×5 cm) and each product was compressed for 15 seconds at 100 pounds per square inch ("psi") using a Machine Solutions stent crimper.

TABLE 4

Experimental results showing that the present elongated expandable member can be compressed to a smaller outer diameter than a commercially available foam product.

| Product | Compressed Diameter (inches) |
| --- | --- |
| Elongated expandable member | 0.047 |
| Pfizer's GELFOAM ® product | 0.052 (approximately 11% larger than the elongated expandable member) |

5. Experiment 5:

In this experiment, a swell ratio and time of an elongated expandable member was explored relative to a swell ratio and time of Pfizer's GELFOAM® product. The swell ratio is defined as the comparison of a volume for a pre-wetted compressed sponge of each product to the post-wetted sponge in 37 degree Celsius saline.

TABLE 5

Experimental results showing that the present elongated expandable member includes a higher swell ratio and lower swell time than a commercially available foam product.

| | Pre-Wetted | Post-Compression | Post-Wetted | % of Volume | Time to Reach Stable Size |
| --- | --- | --- | --- | --- | --- |
| Elongated expandable member | 1 cm × 1 cm × 5 cm | 0.047 inch diameter | 1 cm × 1 cm × 5 cm | 100% | less than 4 seconds |
| Pfizer's GELFOAM ® product | 1 cm × 1 cm × 5 cm | 0.052 inch diameter | 0.84 cm × 0.86 cm × 4.66 cm | 67% | 10 minutes |

Closing Notes:

Over 40 million people in the U.S. alone have varicose veins and suffer from the aching, pain, leg heaviness and swelling, fatigue, and aesthetic issues associated with the disease. Advantageously, the present assemblies, kits, and methods can provide a varicose vein treatment and delivery and implant structures that are associated with minimal patient discomfort and a minimal risk of vessel perforation, are mechanically stable, resist migration and are cosmetically pleasing, do not require a capital equipment investment or vein insulation, and form part of a procedure that can be completed in a relatively fast manner.

Upon in situ separation and removal of an impermeable outer member of an assembly, a compressed elongated expandable member is allowed to radially expand inside a target vein, for example, by absorbing fluid such as blood and thereby provide mechanical fixation in and occlusion of the vein. The elongated expandable member can include a gelatin or collagen material configured to have a relatively low density, large pore size, high degree of cross-linking, basic pH level, large compression ratio, and fast swell time when wetted. These properties can allow the elongated expandable member to be implanted through a small access hole, quickly expand and tightly affix itself to a particular location within the target vein without concern of migration, and occlude the target vein for a period of at least 20 days.

The above Detailed Description includes references to the accompanying drawings, which form a part of the Detailed Description. The drawings show, by way of illustration, specific embodiments in which the present assemblies, kits, and methods can be practiced. These embodiments are also referred to herein as "examples."

The above Detailed Description is intended to be illustrative, and not restrictive. For example, the above-described examples (or one or more elements thereof) can be used in combination with each other or used for occluding or sealing other non-vascular structures, such as a lung or kidney void following a biopsy. Other embodiments can be used, such as by one of ordinary skill in the art upon reviewing the above description. Also, various features or elements have been grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount. In this document, the terms "proximal" and "distal" are used to refer to an assembly element location relative to a caregiver user. For example, a proximal element portion is a portion closer to the caregiver user of the assembly, whereas a distal element portion is a portion farther away from the caregiver user of the assembly, such as the portion interacting with a patient. In this document, the term "patient" is meant to include mammalian bodies, such as for human applications or veterinary applications. Finally, in this document, the term "separation" or "tear-away" is intended to include removal of a member by splitting, peeling, cutting and the like along a split, cut line, score line, linear orientation, or other structure allowing longitudinal separation of the member's material.

In the appended claims, the terms "including" and "in which" are used as the plain-English equivalents of the respective terms "comprising" and "wherein." Also, in the following claims, the terms "including" and "comprising" are open-ended, that is, an assembly, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. An assembly, comprising:
   a removable inner member, the inner member including a handle coupled to a proximal end portion;
   a removable outer member, the outer member including an impermeable material; and
   an elongated expandable member, including a gelatin material or a collagen material having a degree of vapor cross-linking characterized by Lysine residuals of 1.5% or less, positioned in a compressed form between a longitudinal inner surface of the outer member and a longitudinal outer surface of the inner member,
   the elongated expandable member longitudinally positionable in alignment within a portion of the natural flow duct of a vascular vessel and configured to expand and occlude the duct of the vascular vessel following in situ separation and removal of the outer member.

2. The assembly of claim 1, wherein the degree of cross-linking is configured to prevent the gelatin or collagen material from degrading for a period of at least 20 days.

3. The assembly of claim 1, wherein the elongated expandable member includes a density between 0.005 g/cm$^3$ and 0.010 g/cm$^3$.

4. The assembly of claim 1, wherein the elongated expandable member includes a wicking agent selected from a salt or a sugar.

5. The assembly of claim 1, wherein the elongated expandable member is configured to expand, when wetted, from a compressed first diametrical size to a second larger diametrical size, the second larger diametrical size at least 5 times the first diametrical size.

6. The assembly of claim 5, wherein the elongated expandable member includes a length of at least 10 centimeters, and wherein the elongated expandable member completely expands in situ from the first diametrical size to the second larger diametrical size within a time period of 5 minutes or less.

7. The assembly of any one of claim 5 or 6, wherein the second larger diametrical size of the elongated expandable member is substantially equal to a pre-wetted size of the member before being compressed and positioned between the longitudinal inner surface of the outer member and the longitudinal outer surface of the inner member.

8. The assembly of claim 1, wherein the elongated expandable member includes an antimicrobial agent selected from a silver compound, chlorhexidine, an antibiotic, or an iodine-containing agent.

9. The assembly of claim 1, wherein the elongated expandable member includes a pH adjuster in a concentration that results in the member having a pH greater than 5.7, the pH adjuster selected from hydrochloric acid, sodium hydroxide, or a buffer.

10. The assembly of claim 1, wherein the outer member includes a handle, configured to detachably couple to the handle of the inner member, at a proximal end portion.

11. The assembly of claim 1, wherein the elongated expandable member includes a drug having a property of promoting tissue in-growth to accelerate vascular vessel closure.

* * * * *